US005616772A

United States Patent [19]

O'Neill et al.

[11] Patent Number: 5,616,772
[45] Date of Patent: Apr. 1, 1997

[54] METHOD OF STABILIZING NITRILES

[75] Inventors: Gerald J. O'Neill, Arlington, Mass.; Albert H. Levesque, Nashua, N.H.

[73] Assignee: Hampshire Chemical Corp., Lexington, Mass.

[21] Appl. No.: 466,095

[22] Filed: Jun. 6, 1995

[51] Int. Cl.$^6$ ................................................. C07C 409/00
[52] U.S. Cl. ................................................. 558/304
[58] Field of Search ................................................. 558/304

[56] References Cited

U.S. PATENT DOCUMENTS

| | | | |
|---|---|---|---|
| 2,175,805 | 10/1939 | Jacobson | 558/304 |
| 2,590,072 | 3/1952 | Drew et al. | 558/304 |
| 3,061,628 | 10/1962 | Singer et al. | 260/465.5 |
| 3,504,011 | 3/1970 | Gandhi et al. | 260/465.5 |
| 3,515,742 | 6/1970 | Morgan et al. | 260/465.5 |
| 3,988,360 | 10/1976 | Gaudett et al. | 260/465.5 |
| 4,560,516 | 12/1985 | Singer | 260/465.5 |
| 4,895,971 | 1/1990 | Su et al. | 558/346 |
| 4,933,487 | 6/1990 | Hoelderich et al. | 560/205 |
| 5,097,072 | 3/1992 | O'Neill et al. | 564/491 |

*Primary Examiner*—Johann Richter
*Assistant Examiner*—Ebenezer Sackey
*Attorney, Agent, or Firm*—Nields & Lemack

[57] ABSTRACT

A method of stabilizing nitriles, and in particular iminodiacetonitrile (IDAN), ethylendiamine-triacetonitrile (EDTN), and especially nitrilotriacetonitrile (NTAN). The present invention also encompasses the resulting stabilized nitrile. The method of the present invention comprises contacting the nitrile with a mixture of silica and alumina, zeolites or glass.

10 Claims, No Drawings

METHOD OF STABILIZING NITRILES

BACKGROUND OF THE INVENTION

Nitrilotriacetonitrile (NTAN) is a well known intermediate in the preparation of nitrilotriacetic acid (NTA) and salts thereof, which are useful as sequestering agents in detergents, etc. Typical processes for producing NTAN are disclosed in U.S. Pat. No. 3,504,011, U.S. Pat. No. 3,515,742 and U.S. Pat. No. 3,061,628.

Nitriles can polymerize, depending upon the pH. They can also spontaneously eliminate HCN, or there can be residual cyanide present in the nitrile from its preparation. Indeed, one of the methods of NTAN preparation is in accordance with the following general equation, wherein HCN is a reactant:

$$NH_3 + 3HCHO + 3HCN \rightarrow N(CH_2CN)_3$$

Similarly, HCN can itself polymerize, as can the nitrile residue of the HCN elimination. These phenomena are accelerated by heat, depending on the structure of the nitrile.

A particular problem is presented with solid nitriles when the same are heated in solution. Specifically, a slow degradation takes place, marked by gradually increasing discoloration of the solution, until the solution becomes dark brown or black with the eventual appearance of solids. Where such a solution is to be used as feedstock for a hydrogenation process to convert the nitrile to an amine or some intermediate, such as is disclosed in U.S. Pat. No. 5,097,072, the metal catalyst that is typically used in such a process quickly becomes inactive. It is believed that the catalyst is poisoned either by cyanide or by cyanide and nitrile polymers. Once so poisoned, the catalyst cannot be reactivated.

It is therefore an object of the present invention to provide a means for the stabilization of nitriles, and in particular, NTAN.

It is a further object to avoid rapid deactivation of catalyst by stabilizing nitrile reactants.

SUMMARY OF THE INVENTION

The problems of the prior art have been overcome by the present invention, which provides a method of stabilizing nitriles, and in particular iminodiacetonitrile (IDAN), ethylenediamine-triacetonitrile (EDTN), and especially nitrilotriacetonitrile (NTAN). The present invention also encompasses the resulting stabilized nitrile. In general terms, the method of the present invention comprises contacting the nitrile with a mixture of silica and alumina, zeolites or glass.

DETAILED DESCRIPTION OF THE INVENTION

The nitrile that is appropriate for stabilization in accordance with the present invention can be made by any suitable means. For example, NTAN and IDAN can be formed by reacting hexamethylenetetramine, formaldehyde and hydrogen cyanide as disclosed in U.S. Pat. Nos. 3,061,628, 3,504,011, 3,988,360 and 4,895,971, the disclosures of which are hereby incorporated by reference.

Degradation of the nitrile can be demonstrated by comparing Gardner color. The effects of concentration, temperature and time on the degradation of NTAN in DMAC are shown in Table 1. Solutions of NTAN in DMAC were placed in stainless steel cylinders and stored in a heated oven without agitation. Samples were removed from the cylinders at various time intervals and their colors measured against the Gardner scale. Once an NTAN/DMAC solution has reached a Gardner color of 3–4, a negative effect can be seen on catalyst activity.

TABLE 1

| Degradation of NTAN in Heated DMAC | | | |
|---|---|---|---|
| NTAN Conc'n % | Temp. °C. | Elapsed Time (hours) | Gardner Color |
| 35 | 60 | 25 | 4 |
|  |  | 97 | 9 |
|  |  | 121 | 12 |
|  |  | 169 | 13 |
| 40 | 93 | 0 | <1 |
|  |  | 1 | 2 |
|  |  | 2 | 3 |
|  |  | 3 | 4 |
|  |  | 4 | 5 |
|  |  | 5.5 | 6 |
|  |  | 6.5 | 6 |
|  |  | 7.5 | 7 |
|  |  | 71.5 | 16 |

The hydrogenation of a wide variety of nitriles, especially of NTAN, IDAN and EDTN, to their corresponding amines using conventional hydrogenation catalysts often provides the desired noncyclic products in low selectivity and yield. Adjusting reaction conditions to improve selectivity or yield can result in rapid inactivation of the catalyst materials used. The effect of storage time of preheated nitrile on catalyst activity can be demonstrated by comparing yields in such a hydrogenation reaction, as between nitrile that has been stabilized according to the present invention, and nitrile that has not been so stabilized. Specifically, solutions of 40% NTAN in DMAC were heated at 100° C. for increasing periods of time and then hydrogenated to form tris (2-aminoethyl) amine (TREN) in a high pressure autoclave over Raney® cobalt catalyst. Reaction conditions were 1000 psig hydrogen, 125° C., space velocity of 1 and $NH_3$/NTAN mole ratio of 2.6. The runs were conducted in a recycle mode to simulate actual practice. The results are shown in Table 2.

TABLE 2

| Effect of Preheating of (40%) NTAN Feedstock on TREN Yield | | |
|---|---|---|
| Preheat Time (hrs.) | Temp. (°C.) | TREN Yield |
| 48 | 100 | 40.4 |
| 48 | 100 | 22.5 |
| 65 | 100 | 0 |

The foregoing data indicates t-he partial and eventual complete inactivation of catalyst.

The inventors of the present invention have found that $SiO_2$ and $Al_2O_3$ do not significantly enhance the stability of the nitriles when used alone. Surprisingly, however, when a combination of silica and alumina is used, significant stabilization of the nitriles is achieved. Other suitable stabilizers in accordance with the present invention include zeolites (or aluminasilicates) and glass, although the combination of silica and alumina is particularly preferred. Preferably the ratio of silica to alumina is such that silica is present in an amount greater than about 25%, prferably greater than 50%, most preferably such that the ratio of $SiO_2:Al_2O_3$ is 75:25 or greater. The particular form of the stabilizer is not critical; powder, pellets, and small particles (8–12 or 14–18 mesh prills) can be used.

When stabilizing iminodiacetonitrile, the preferred stabilizer is acidic alumina ($Al_2O_3$).

The stabilizer can be used in an amount as low as about 1% by weight of the nitrile in solution, although higher amounts are preferred, such as about 5% by weight, in order to achieve greater stabilization effects.

The following examples are given for illustrative purposes and are not meant to be a limitation on the present invention as defined by the claims appended hereto.

EXAMPLE 1

Silica, alumina, zeolite, and various combinations and forms of silica and alumina were placed in solutions of 40% NTAN in DMAC in stainless steel cylinders and placed in a heated oven at 80° C. Samples were removed at various time intervals and their colors measured against the Gardner scale. The results are shown in Table 3:

TABLE 3

Effect of Stabilizers on the Degradation of 40% NTAN/DMAC at 80° C.

| Stabilizer | Time | Gardner Color | Physical Form |
|---|---|---|---|
| $SiO_2$ | 168 | 6 | Silica gel |
| | 394 | 11 | 8–12 mesh |
| | 528 | 16 | |
| $SiO_2$ 87/$Al_2O_2$ 13 | 0 | <1 | Powder |
| | 288 | 1 | |
| $SiO_2$ 75/$Al_2O_3$ 25 | 0 | <1 | 14–18 mesh prills |
| | 72 | <1 | |
| | 168 | 1 | |
| | 312 | 1 | |
| | 648 | 2 | |
| $SiO_2$ 53/$Al_2O_3$ 45 | 168 | 3 | ¼" × ⅛" pellets |
| | 384 | 4 | |
| | 528 | 5 | |
| $SiO_2$ 53/$Al_2O_3$ 47 | 0 | <1 | 14–18 mesh prills |
| | 120 | <1 | |
| | 168 | <1 | |
| | 264 | 2 | |
| | 600 | 3 | |
| $SiO_2$ 37/$Al_2O_3$ 63 | 120 | 1 | 14–18 mesh prills |
| $SiO_2$ 6/$Al_2O_3$ 91 | 120 | 4 | ¼" × ⅛" pellets |
| | 264 | >18 | |
| $Al_2O_3$ | 72 | 3 | Powder |
| | 120 | 5 | |
| | 168 | 6 | |
| | 240 | 8 | |
| | 288 | 12 | |
| | 432 | black | |
| Zeolite | 0 | <1 | 8–12 mesh |
| | 96 | 2 | |
| | 144 | 3 | |
| | 192 | 3 | |

The results shown in Table 3 indicate that neither $SiO_2$ nor $Al_2O_3$ were satisfactory stabilizers when used alone, but any combination of the two had some effect, with combinations having at least 75% $SiO_2$ being the most effective.

EXAMPLE 2

Solutions of 40% NTAN in DMAC were made containing stabilizers selected from those shown in Table 3, and were stored at 80° C. All of the samples were stored for 24 hours at 80° C. before use, and were maintained at that temperature for the duration of that series of runs. The solutions were then hydrogenated under the conditions described above regarding Table 2. The results are shown in Table 4. The Gardner colors shown are those existing at the completion of that series of runs.

TABLE 4

Effect of Feedstock Stabilizers on TREN Yields

| Stabilizer | wt/wt (%) | No of Runs | Total Heating Time (hrs)* | Gardner Color | Av. TREN Yield (%) |
|---|---|---|---|---|---|
| $SiO_2$ 37/$Al_2O_3$ 63 | 5 | 5 | 120 | 1 | 64.7 |
| $SiO_2$ 75/$Al_2O_3$ 25 | 5 | 5 | 168 | 1 | 67.3 |
| $SiO_2$ 53/$Al_2O_3$ 45 | 5 | 5 | 216 | 3 | 63.8 |
| $SiO_2$ 53/$Al_2O_3$ 45 | 2.5 | 5 | 168 | <1 | 65.4 |
| $SiO_2$ 53/$Al_2O_3$ 45 | 1.0 | 5 | 216 | 2 | 64.2 |

*All feedstocks consisted of 40% NTAN in DMAC and were heated for 24 hours at 80° C. before the first run of a series. They were kept at that temperature until the completion of the particular series.

Table 4 shows how the presence of stabilizers in the heated NTAN/DMAC feedstock prevent nitrile degradation and the consequent inactivation of the catalyst. The amount of stabilizer present is shown as a percentage of the weight of NTAN in the solution. Amounts as low as one percent by weight are effective, although higher amounts are preferred.

EXAMPLE 3

To a 40% solution of NTAN, 600 ppm, 1100 ppm and 1000 ppm of HCN was added. Stabilizer was added to the 1100 ppm and 1000 ppm batches, and the solutions were then used as feedstocks to produce TREN under the conditions set forth above in Table 2. The results are shown in Table 5. The results demonstrate that the stabilizers are also effective against free cyanide, which, in many instances, is a catalyst poison. Feedstock to which 600 ppm of HCN but no stabilizer had been added gave a lower than normal yield and inactivated the catalyst after a single run. Improved yields were achieved with even higher amounts of HCN when stabilizer was present.

TABLE 5

Effect of Stabilizer on Free HCN in Feedstock

| HCN Added (ppm) | Stabilizer | No. of Runs | Av. TREN Yield (%) |
|---|---|---|---|
| 600 | None | 2 | 26.8* |
| 1100 | $SiO_2$ 75/$Al_2O_3$ 25 | 6 | 64.0 |
| 1000 | $SiO_2$ 75/$Al_2O_3$ 25 | 5 | 64.9 |

*Actual yields for the 2 runs were 53.2% and 0.

EXAMPLE 4

Acidic $Al_2O_3$ (10 wt %) was placed in a stainless steel cylinder with a 40% solution of IDAN in DMAC. The cylinder was placed in an oven and heated at 55° C. Samples were removed at various time intervals and their color measured against the Gardner scale with the following results:

| Elapsed Time (hrs) | Gardner Color |
|---|---|
| 0 | <1 |
| 48 | 1 |
| 72 | 1 |
| 96 | 1 |
| 168 | 1 |
| 216 | 1 |
| 360 | 2 |

What is claimed is:

1. A method of stabilizing nitriles, comprising contacting said nitriles with a stabilizer selected from the group consisting of a combination of silica and alumina, silica and zeolites, and silica and glass.

2. The method of claim 1, wherein the ratio of silica to alumina in said combination of silica and alumina is 75:25.

3. The method of claim 1, wherein the ratio of silica to alumina in said combination of silica and alumina is 87:13.

4. The method of claim 1, wherein the ratio of silica to alumina in said combination of silica and alumina is 37:63.

5. The method of claim 1, wherein the nitrile is selected from the group consisting of nitrilotriacetonitrile, iminodiacetic nitrile, and ethylenediaminetriacetonitrile.

6. The method of claim 1, wherein the nitrile is nitrilotriacetonitrile.

7. A method of stabilizing iminodiacetonitrile, comprising contacting said iminodiacetonitrile with acidic $Al_2O_3$.

8. Nitrilotriacetonitrile, stabilized according to the method of claim 1.

9. Ethylenediaminetriacetonitrile, stabilized according to the method of claim 1.

10. Iminodiacetonitrile, stabilized according to the method of claim 7.

* * * * *